United States Patent [19]

Srisathapat et al.

[11] Patent Number: 5,466,218
[45] Date of Patent: Nov. 14, 1995

[54] METHOD OF CLEANING AN IMPLANTED MEDICATION INFUSION PUMP WITH DISCHARGE SIDE PORT

[75] Inventors: Chad Srisathapat, Sun Valley; Virote Indravudh, Saugus, both of Calif.

[73] Assignee: MiniMed, Inc., Sylmar, Calif.

[21] Appl. No.: 401,177

[22] Filed: Mar. 9, 1995

Related U.S. Application Data

[62] Division of Ser. No. 221,569, Apr. 1, 1994.

[51] Int. Cl.[6] .............................. A61M 31/00; A61K 9/22
[52] U.S. Cl. ............................................ 604/49; 604/892.1
[58] Field of Search ........................... 604/890.1, 892.1,
604/93, 174, 175, 283, 131, 132, 133, 151,
153, 246, 247, 49, 52, 53

[56] References Cited

U.S. PATENT DOCUMENTS

| | | | |
|---|---|---|---|
| H150 | 11/1986 | Hankner et al. | 604/93 |
| 4,373,527 | 2/1983 | Fischell | 604/93 X |
| 4,573,994 | 3/1986 | Fischell et al. | 604/93 X |
| 4,697,622 | 10/1987 | Swift et al. | 141/1 |
| 5,257,971 | 11/1993 | Lord et al. | 604/49 |
| 5,370,635 | 12/1994 | Strausak et al. | 604/248 |

Primary Examiner—Corrine M. Maglione
Assistant Examiner—Adam J. Cermak
Attorney, Agent, or Firm—Kelly Bauersfeld & Lowry

[57] ABSTRACT

A medication infusion pump is provided of the type adapted for implantation into the body of a patient, and for programmable delivery of a selected medication through a catheter to the patient over an extended period of time. A side port assembly is mounted quickly and easily onto the pump and defines a flow path through which the medication is discharged to the catheter. The side port assembly includes an access port to permit transcutaneous needle access to the discharge flow path, in combination with a check valve to prevent backflow within the discharge flow path. The discharge side access port can be used to flush residue from the catheter, or in combination with a primary refill port on the pump to flush the pump and/or to determine actual pump stroke volume.

1 Claim, 3 Drawing Sheets

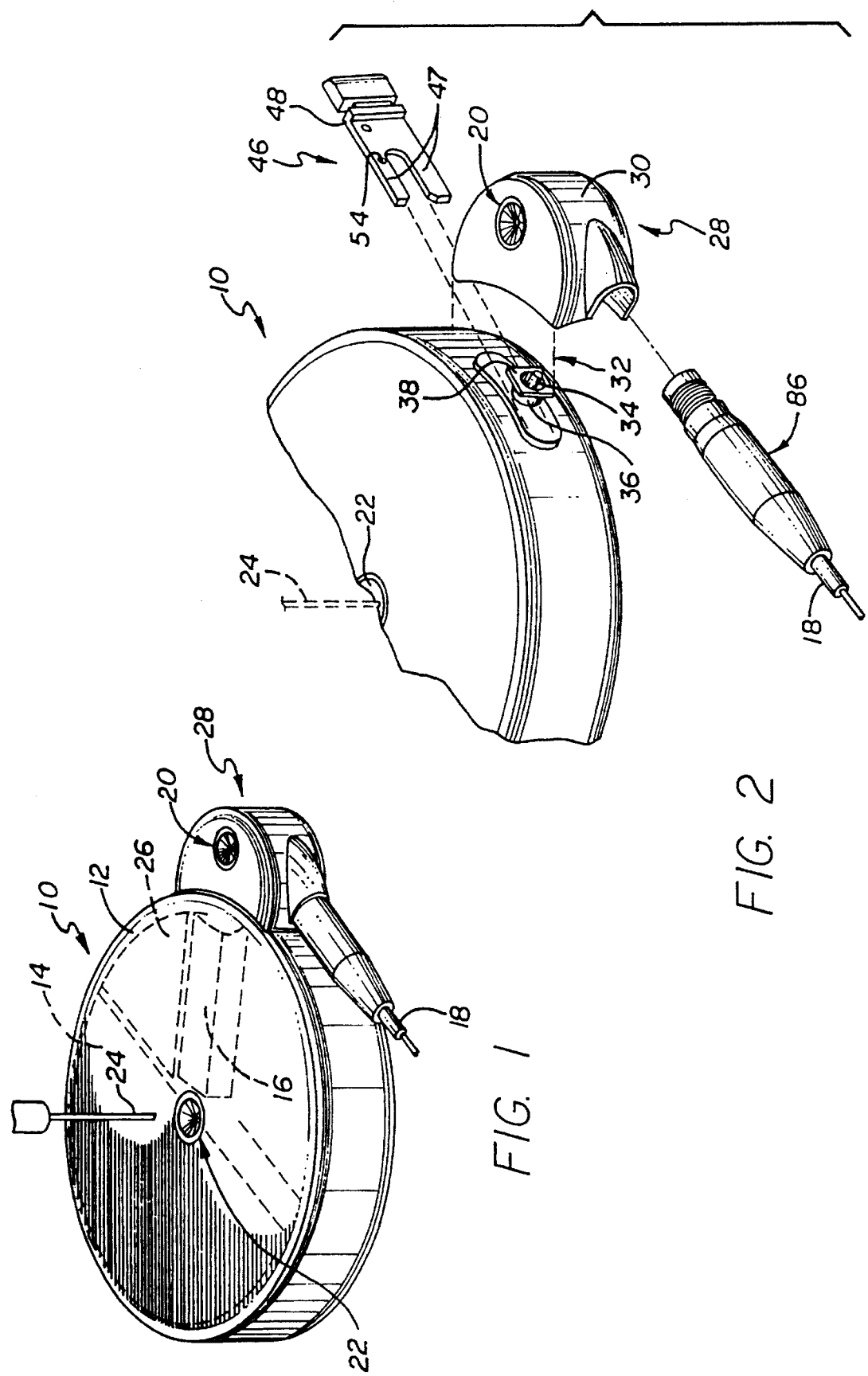

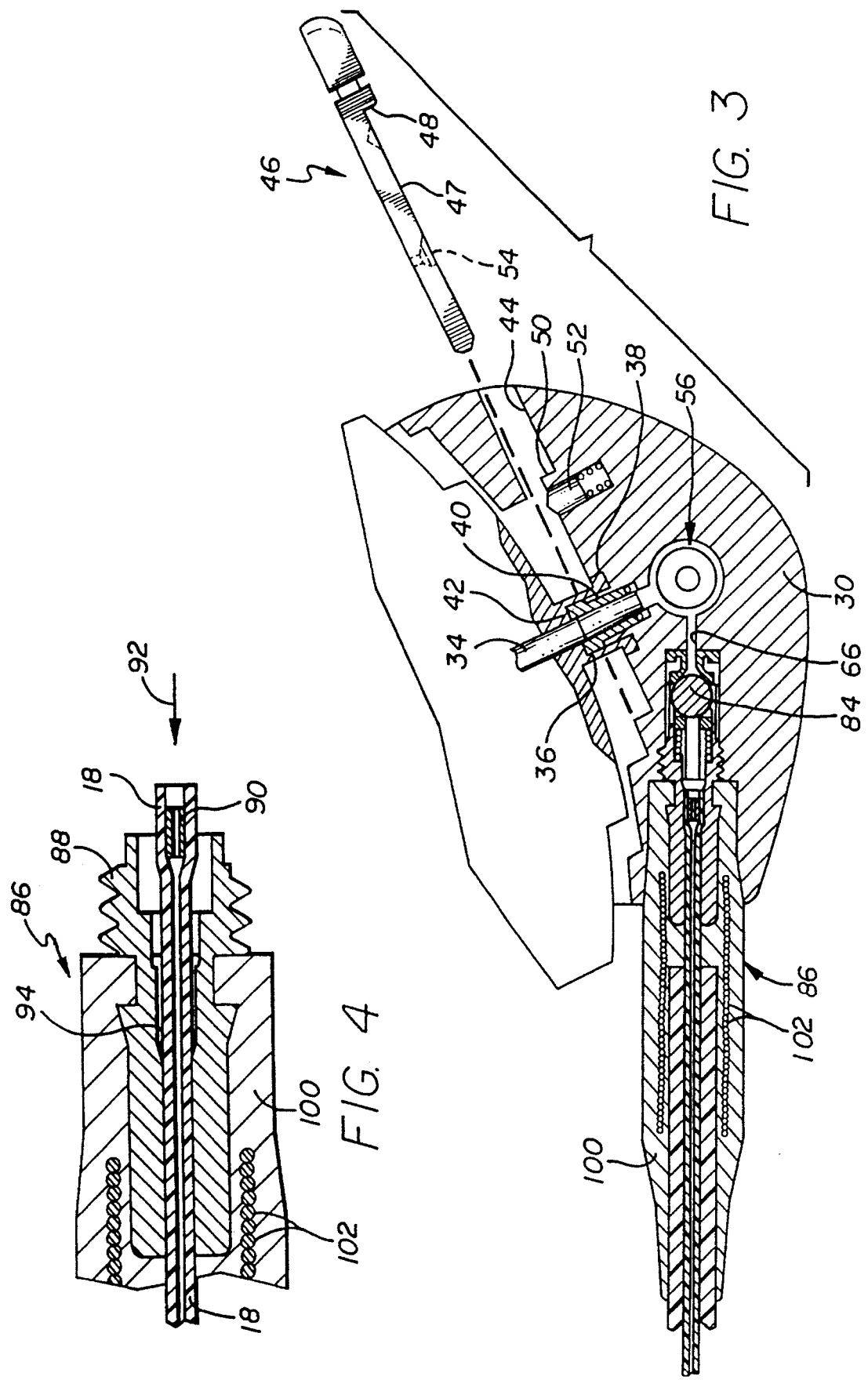

METHOD OF CLEANING AN IMPLANTED MEDICATION INFUSION PUMP WITH DISCHARGE SIDE PORT

This is a division of application Ser. No. 08/221,569, filed Apr. 1, 1994.

BACKGROUND OF THE INVENTION

This invention relates generally to medication infusion pumps, particularly of the type adapted for implantation directly into the body of a patient and for programmed operation to deliver a selected medication through a catheter to the patient over an extended period of time. More specifically, this invention relates to an improved implantable infusion pump having a discharge side access port which can be used to clean or flush residue from the pump and/or within the catheter.

Medication infusion pumps are generally known in the art for use in delivering a selected medication to a patient in a scheduled or preprogrammed manner. In recent years, infusion pumps have been developed in compact form and adapted for direct implantation into the body of a patient, to deliver a specific medication such as insulin to the patient in discrete doses over an extended period of time. An implantable infusion pump of this general type includes an internal medication chamber or reservoir for receiving and storing a supply of the selected medication in liquid form, in combination with a miniature pump mechanism and associated programmable control means for operating the pump mechanism to deliver discrete doses of the medication from the internal storage reservoir and through a catheter to the patient. A refill port is provided on the pump to permit transcutaneous needle access for purposes of periodically refilling the pump reservoir with a fresh supply of medication. For one illustrative example of an implantable medication infusion pump of this general type, see U.S. Pat. No. 4,573,994.

Implantable and programmable medication infusion pumps offer significant potential advantages to patients who are required to comply with a long term medication treatment regimen. Such implantable pumps can operate automatically, with little or no patient intervention, to administer an important medication such as insulin to a diabetic patient on a regular basis.

However, it is known that particle-like residues can accumulate over a period of time within the pump mechanism and the related discharge catheter of an implantable infusion pump. Such residues are believed to be the result of shear denaturation and/or precipitation of pharmaceutical components, especially in the case of relatively complex molecule and/or protein-based medications such as insulin and the like. These particle-like residues can collect in sufficient quantity to reduce the medication stroke volume of the pump mechanism and, in some cases, to occlude the discharge catheter.

Various techniques have been proposed to flush accumulated residues from the flow passages associated with an implantable medication infusion pump. For example, it is known to inject a suitable cleaning agent into the pump reservoir, and then operate the pump in a manner to circulate the cleaning agent through pump flow passages and through the discharge catheter in an effort to dissolve and/or dislodge accumulated residues. This technique, however, undesirably results in ultimate delivery of the cleaning agent to the patient.

There exists, therefore, a significant need for further improvements in implantable medication infusion pumps, particularly with respect to devices and methods for permitting accumulated residues within pump flow passages to be removed, in a manner which does not require delivery of cleaning agents to the patient. The present invention fulfills these needs and provides further related advantages.

SUMMARY OF THE INVENTION

In accordance with the invention, an improved implantable medication infusion pump is equipped with a side port assembly for use in cleaning or flushing accumulated particle-like residues from internal pump flow passages. The side port assembly defines a discharge flow path adapted for connection between a pump outlet port and a catheter through which a selected medication is delivered to a patient. The side port assembly further includes a discharge side access port which permits transcutaneous access to the discharge flow path, in combination with a discharge side check valve to prevent backflow within the discharge flow path. The discharge side access port conveniently permits accumulated residues to be flushed from the catheter. Alternately, the discharge side access port may be used in combination with a primary refill port on the pump to clean and flush internal pump flow passages by pump circulation of a cleaning agent delivered through the primary refill port and by withdrawing that cleaning agent through the discharge side access port.

In accordance with a preferred form of the invention, the implantable infusion pump includes the pump outlet port through which medication is delivered from a pump housing. The side port assembly has a slide-fit fitting for engaging the pump outlet port in flow communication with the discharge flow path. A lock clip is slidably seated within an open-sided slot formed in the side port assembly to engage a flanged mounting lug on the pump housing to retain the side port assembly on said pump housing.

The discharge flow path defined by the side port assembly is in flow communication with the discharge side access port adapted for transcutaneous needle access therewith. From the side access port, the discharge flow path extends in flow communication with the catheter mounted conveniently onto the side port assembly by means of a strain relief fitting.

The discharge side access port permits cleaning or flushing of residue from the catheter, by introducing an appropriate liquid under pressure for flush flow passage through the catheter. In addition, a selected cleaning agent may be introduced into the pump by means of the primary refill port, wherein that cleaning agent can be pumped through the infusion pump to dissolve and/or dislodge residue. In this case, cleaning agent and entrained residue pumped through the outlet port can be withdrawn from the patient through the discharge side access port, thereby preventing delivery of any significant quantity of the cleaning agent to the patient. Still further, fluid discharged from the pump can be withdrawn via the discharge side access port and measured to obtain an accurate determination of actual current pump stroke output volume.

Other features and advantages of the present invention will become more apparent from the detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating an implantable medication infusion pump equipped with a side port assembly in accordance with the novel features of the invention;

FIG. 2 is a fragmented exploded perspective view depicting connection of the side port assembly onto the implantable infusion pump;

FIG. 3 is an enlarged fragmented and partially exploded sectional view showing internal construction details of the side port assembly;

FIG. 4 is an enlarged fragmented sectional view illustrating assembly of a catheter with a strain relief fitting for use in the invention;

DETAILED DESCRIPTION OF THE PREFERRED EMBODIMENT

Figure 5:
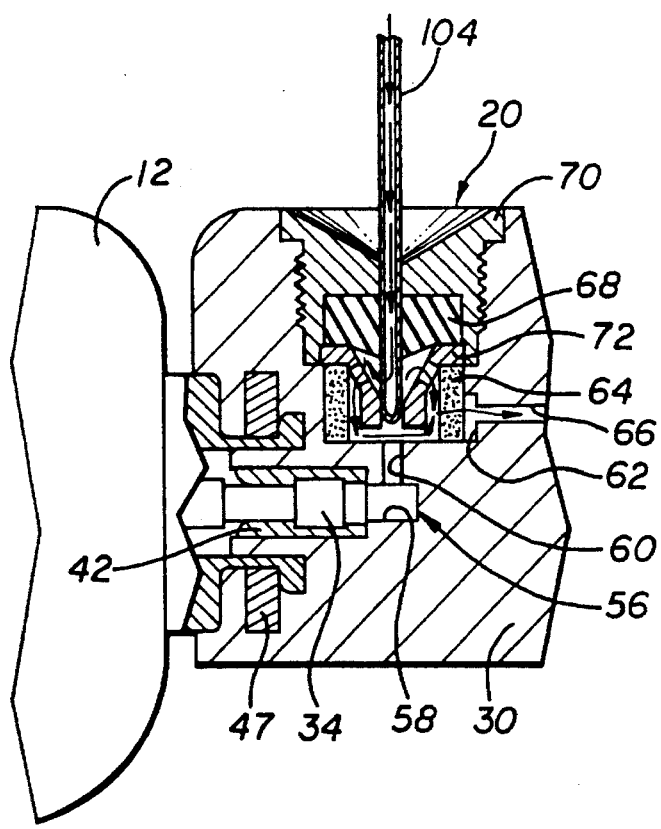
FIG. 5 is an enlarged fragmented and somewhat schematic sectional view depicting use of the side port assembly to flush residue from the catheter.

As shown in the exemplary drawings, a medication infusion pump referred to generally in FIG. 1 by the reference numeral 10 is provided for direct implantation into the body of a patient (not shown). The pump 10 comprises a substantially sealed housing 12 encasing a medication storage reservoir 14 and an appropriate pump mechanism 16 for delivering discrete doses of a selected medication through a catheter 18 to a patient. In accordance with the invention, the pump 10 is equipped with a discharge side access port 20 which can be used to flush or clean accumulated particle-like residues from the catheter 18, and/or from internal pump flow passages.

The illustrative medication infusion pump 10 comprises a compact and substantially self-contained unit adapted for direct implantation into the body of a patient. The pump housing 12 comprises an hermetically sealed case formed from a biocompatible material, typically such as titanium or titanium alloy. A primary inlet or refill port 22 is provided on the pump housing 12 to receive a hypodermic needle 24 to permit transcutaneous refilling of the medication storage reservoir 14 within the pump housing. During normal operation, the pump mechanism 16 within the housing 12 is programmably operated by an appropriate control circuit 26 to deliver the medication via the catheter 18 in accordance with individual patient requirements. For a more detailed description of the overall construction and operation of implantable infusion pumps of this general type, including the construction of the refill port 22, see U.S. Pat. Nos. 4,373,527 and 4,573,994 which are incorporated by reference herein.

Over a period of time, particle-like medication deposits can accumulate within the catheter 18, and also within internal flow passages of the pump 10. These medication deposits are believed to consist primarily of protein and other organic constituents, particularly when relatively complex and/or protein-based medications such as insulin are used. These accumulated deposits can eventually interfere with accurate pump operation and, in some instances, occlude the catheter 18.

A compact side port assembly 28 is provided in accordance with the present invention, wherein the side port assembly 28 includes the discharge side access port 20. As will be described in more detail, this discharge side access port 20 permits facilitated flushing of particle-like deposits from the catheter 18. In addition, the side access port 20 can be used in combination with the primary refill port 22 to flush and clean residue from internal pump flow passages.

As shown best in FIGS. 2 and 3, the side port assembly 28 comprises a relatively small, substantially half-circle case or shell 30 adapted for facilitated interconnection between a pump outlet port 32 and the catheter 18. As shown, the pump outlet port 32 includes a discharge tube 34 which projects outwardly a short distance from one edge of the pump housing 12, and disposed within a generally cylindrical mounting lug 36 having a flanged end 38. The side port assembly has an inboard side or face adapted for flush-fit mounting against the side edge of the pump housing 12. A cylindrical slide-fit fitting 40 including one or more seal members 42 therein is provided on the side port assembly for slide-fit sealed engagement about the discharge tube 34, within the mounting lug 36. In this position, a transversely open slot 44 formed in the housing shell 30 is aligned generally with the mounting lug 36, at a location behind the flanged end 38. A fork-shaped lock clip 46 includes a pair of generally parallel legs 47 for slide-fit reception through the slot 44, behind the flange lug end 38, for locking the side port assembly onto the pump housing 12. As shown best in FIG. 3, the lock clip 46 is advanced into the slot 44, until a shoulder 48 thereon engages a stop 50, at which time a spring-loaded detent pin 52 is seated within a shallow detent 54 in one leg 47 of the lock clip 46.

Figure 6:
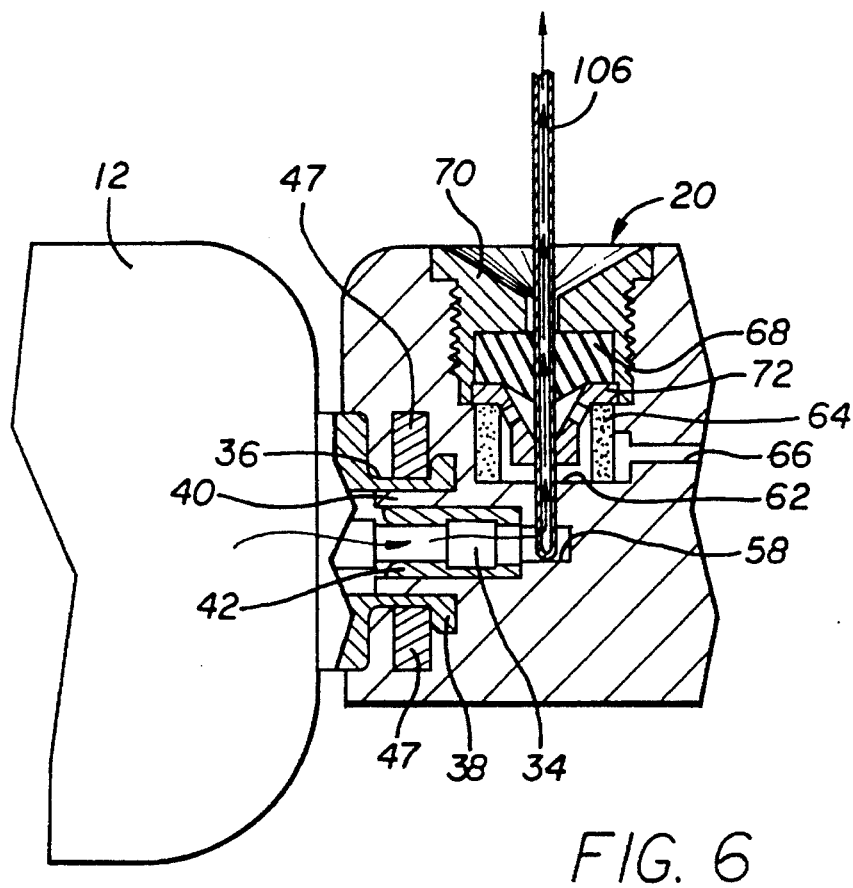
FIG. 6 is an enlarged fragmented and somewhat diagrammatic sectional view similar to FIG. 5, and showing use of the side port assembly in flushing accumulated residue from internal flow passages of the implantable infusion pump.

With the side port assembly 28 mounted onto the pump housing 12, as described, the pump discharge tube 44 is placed in flow communication with a discharge flow passage 56 of the side port assembly. More particularly, as shown in FIGS. 5 and 6 in the exemplary drawings, the discharge tube 34 opens into a small chamber 58 which communicates via a narrow port 60 with an overlying filter chamber 62. An annular filter 64 is seated within the filter chamber 62 and accommodates passage of the medication therethrough to a catheter passage 66 leading to the catheter 18, as will be described in more detail.

The discharge side access port 20 includes a self-sealing resilient septum 68 formed from a suitable elastomer material and trapped between an overlying port shield 70 and an underlying needle retainer 72. More particularly, the port shield 70 defines an upwardly presented concave depression of generally conical shape suitable for tactile identification and having a needle port at the lower apex end thereof. The exterior of the port shield 70 is threaded for appropriate thread-in mounting within a threaded bore formed in the shell 30. The septum 68 is axially retained between the underside of the port shield 70 and an annular upper rim of the needle retainer 72. From the rim, the retainer extends downwardly to define another concave depression with a needle port at the lower apex end thereof. A ring of flow apertures are formed in the conical wall of the needle retainer to permit fluid flow between the upper and lower sides of the retainer 72.

As shown in FIG. 3, one side of the filter chamber 62 is in flow communication with the catheter passage 66. This passage 66 is normally closed by a spring loaded check valve 84 such as the illustrative ball valve for preventing fluid backflow toward the pump. The check valve 84 is mounted at the upstream end of a strain relief fitting 86 which has the catheter 18 supported therein. The catheter 18 extends outwardly through the strain relief fitting 86, to a selected medication delivery site within the body of a patient.

FIG. 4 illustrates a preferred means for assembling the catheter 18 with the strain relief fitting 86 in a quick and easy manner, wherein the connection is capable of withstanding substantial fluid pressures without leakage. As shown, an upstream end of the catheter 18 is slidably fitted through the strain relief fitting 86, axially beyond a threaded nipple 88 thereon. A rigid cylindrical sleeve 90 is fitted into the upstream end of the catheter 18, resulting in slight diameter expansion of the resilient catheter material. The catheter 18 is then drawn in the direction of arrow 92 to seat the sleeve 90 in a position wedged within a converging segment 94 of a passage in the strain relief fitting. With this construction, the catheter 18 is tightly secured within the strain relief fitting, in a manner which is not conducive to fluid leakage therebetween.

The strain relief fitting 86 is attached quickly and easily to the side port assembly 28, by thread-in connection of the nipple 88 into a threaded bore formed in the shell 30. From the nipple 88, the strain relief fitting 86 may include a short protective and somewhat flexible outer support tube 100, which may include a reinforcing spiral core 102. This strain relief fitting 86 provides a durable anchored mounting of the catheter 18 with respect to the implantable pump.

FIG. 5 illustrates use of the discharge side access port 20 to flush residue or deposits from the catheter 18. As shown, a hypodermic needle 104 of appropriate gauge is fitted through the needle port in the port shield 70. In this regard, the hypodermic needle 104 is selected for passage through the shield port, but to preclude passage through the needle port in the underlying retainer 72. With this construction, a flush solution can be injected into the side access port 20, for flow under appropriate pressure through the flow apertures in the retainer 72, and further flow passage through the filter 64 and the check valve 84 to the patient. This pressurized flush flow, which may include any solution compatible with delivery to the patient, can be supplied under sufficient pressure as high as 200 psi to dislodge and carry away accumulated residue within the catheter. Thus, the catheter 18 which has become or is suspected to be occluded can be reopened without requiring surgical access to the pump.

FIG. 6 shows utilization of the discharge side access port 20 in flushing or cleaning residue from internal pump passages within the pump 10. In this method, a smaller gauge hypodermic needle 106 is fitted through the side access port 20 to position the end of the needle through and beneath the filter chamber 62 for direct flow communication with the pump discharge tube 34. A second hypodermic needle such as the needle 24 shown in FIGS. 1 and 2 can be fitted through the primary refill port 22 to fill the pump reservoir 14 with a selected cleaning agent. The pump mechanism 16 can then be operated as desired to pump the cleaning agent from the reservoir and through internal pump flow passages to the discharge tube 34. The cleaning agent effluent can be withdrawn from the patient via the hypodermic needle 106 at the discharge side access port 20, whereby the internal pump passages can be thoroughly cleaned without leaving any significant volume of cleaning agent within the pump or otherwise available for delivery to the patient. During this procedure, the check valve 84 prevents backflow through the catheter 18 to the needle 106.

The side access port 16 may also be used as shown generally in FIG. 6 to obtain accurate measurements of actual pump stroke output volume. To this end, the hypodermic needle 106 is fitted as previously described in flow communication with the pump discharge tube 34. The pump 10 can then be operated through a single or multiple strokes to deliver medication through the discharge tube 34. That medication is caused to flow through the hypodermic needle 106 and can be connected to an appropriate measuring pipette or other measuring device, so that accurate pump stroke volume can be determined. Measurement of actual pump stroke volume is, of course, reflective of accumulation of deposits which may have occurred within internal pump flow passages and thus provides an indication of a need to perform additional cleaning procedures as noted above.

A variety of further modifications and improvements to the improved medication infusion pump of the present invention will be apparent to those skilled in the art. Accordingly, no limitation on the invention is intended by way of the foregoing description and accompanying drawings, except as set forth in the appended claims.

What is claimed is:

1. In an implantable medication infusion pump having a pump housing with a medication-receiving reservoir and-pump means for delivering medication through a pump outlet port, a refill port on the pump housing to permit transcutaneous needle access to refill the reservoir with the medication, a catheter coupled to the pump outlet port and cooperating therewith to define a discharge flow path for flow passage of the medication to a patient, and a side access port to permit transcutaneous needle access to the discharge flow path, a method of cleaning the pump without requiring explantation of the pump from the patient, said method comprising the steps of:

operating the pump means to deliver residual medication from the reservoir to the discharge flow path, while aspirating the delivered medication from the patient via a needle coupled through said side access port to the discharge flow path;

delivering a selected cleaning agent to the reservoir via said refill port;

operating the pump means to deliver the cleaning agent from the reservoir to the discharge flow path, while aspirating the delivered cleaning agent from the patient via said side access port; and refilling the reservoir with the medication via said refill port.

* * * * *